United States Patent [19]
Wright et al.

[11] Patent Number: 5,710,713
[45] Date of Patent: *Jan. 20, 1998

[54] METHOD OF CREATING STANDARDIZED SPECTRAL LIBRARIES FOR ENHANCED LIBRARY SEARCHING

[75] Inventors: Larry G. Wright; Mark A. LaPack; Wayne W. Blaser; Kenneth R. Beebe; Mary A. Leugers, all of Midland, Mich.

[73] Assignee: The Dow Chemical Company, Midland, Mich.

[ * ] Notice: The portion of the term of this patent subsequent to Mar. 15, 2015, has been disclaimed.

[21] Appl. No.: 588,192

[22] Filed: Jan. 18, 1996

Related U.S. Application Data

[63] Continuation-in-part of Ser. No. 407,338, Mar. 20, 1995, Pat. No. 5,545,895.

[51] Int. Cl.[6] .................................................. H01J 49/00
[52] U.S. Cl. ....................... 364/498; 250/282; 364/571.02
[58] Field of Search .............................. 364/498, 496, 364/497, 571.01, 571.02, 571.04; 250/252.1, 281, 282; 73/23.21, 23.22, 23.36, 23.37; 436/173

[56] References Cited

U.S. PATENT DOCUMENTS

| | | | |
|---|---|---|---|
| 2,551,637 | 5/1951 | Robinson | 250/252.1 |
| 3,551,658 | 12/1970 | Prater et al. | 235/151 |
| 3,975,727 | 8/1976 | Mader et al. | 340/347 NT |
| 4,008,388 | 2/1977 | McLafferty et al. | 235/151 |
| 4,353,242 | 10/1982 | Harris et al. | 73/23.36 |
| 4,587,624 | 5/1986 | Banno | 364/571 |
| 4,660,151 | 4/1987 | Chipman et al. | 364/497 |
| 4,807,148 | 2/1989 | Lacey | 364/497 |
| 4,847,493 | 7/1989 | Sodal et al. | 250/252.1 |
| 4,864,842 | 9/1989 | Regimand | 73/1 R |
| 4,866,644 | 9/1989 | Shenk et al. | 364/509 |
| 4,916,645 | 4/1990 | Wuest et al. | 364/571.04 |
| 4,974,209 | 11/1990 | Hoult | 364/497 |
| 5,014,217 | 5/1991 | Savage | 364/498 |
| 5,016,203 | 5/1991 | Komatsu et al. | 364/571.02 |
| 5,023,804 | 6/1991 | Hoult | 364/497 |
| 5,072,115 | 12/1991 | Zhou | 250/281 |
| 5,083,283 | 1/1992 | Imal et al. | 364/497 |
| 5,121,337 | 6/1992 | Brown | 364/498 |
| 5,243,546 | 9/1993 | Maggard | 364/571.02 |
| 5,291,426 | 3/1994 | Collins et al. | 364/574 |
| 5,303,165 | 4/1994 | Ganz et al. | 364/571.01 |
| 5,313,406 | 5/1994 | Kauppinen et al. | 364/498 |
| 5,352,891 | 10/1994 | Monnig et al. | 250/282 |
| 5,357,336 | 10/1994 | Ruhl, Jr. et al. | 356/319 |
| 5,459,677 | 10/1995 | Kowalski et al. | 364/571.02 |
| 5,545,895 | 8/1996 | Wright et al. | 250/282 |

OTHER PUBLICATIONS

Onno e. De Noord, "Multivariate calibration standardization", Chemometrics and Intelligent Laboratory Systems, 25 (1994) Nov., No. 2, Amsterdam, NL, pp. 85–97.

Mark et al., *A New Approach to Generating Transferable Calibrations for Quantitative Near–Infrared Spectroscopy*, Spectroscopy, vol. 3, No. 11, pp. 28–36 No Date.

Smith et al., Quantitative Comparison of Combined Gas Chromatographic/Mass Spectro. Profiles of Complex Mixtures, Anal. Chem. 49, 11, 1977–1623–32.

Wang et al., Multivariate Instrument Standardization, Anal. Chem. 63, 1991, 2750–2756.

(List continued on next page.)

*Primary Examiner*—James P. Trammell
*Assistant Examiner*—M. Kemper

[57] ABSTRACT

A method of creating a library of standardized spectral data and identifying a sample by searching the standardized library for a match with the sample spectrum. The method entails determining and applying a transfer function which equalizes instrument bias between instruments and within the same instruments over time. A transfer function is specific to a particular instrument, and is based on the relationship between a reference spectrum of a standard as stored in a library and a spectrum of the standard obtained on the particular instrument of interest. This method provides enhanced library searching capabilities.

11 Claims, 2 Drawing Sheets

OTHER PUBLICATIONS

Wang et al., Improvement of Multivariate Calibration through Instru Standardization, Anal. Chem. 64, 1992, 562–564.

Calibration Pt. for Electron Ionization MS/MS Spectra Measured with Multiquadrupole Mass Spectrometers, 1994 Am. Soc. for Mass Spectrometry, Mohan et al., 576–582 No Month.

Stein et al., Optimization and Testing of Mass Spectral Library Search Algorithms for Compound Identification, J. Am. Soc. Mass Spectrom, 1994, 5, 859,866 No Month.

Int'l Application No. PCT/US92/08547, filed Jul. 10, 1991 Ashland Oil, Inc., Pub. No. 94/08225.

METHOD OF CREATING STANDARDIZED SPECTRAL LIBRARIES FOR ENHANCED LIBRARY SEARCHING

This application is a Continuation-in-Part of U.S. Ser. No. 08/407,338 filed Mar. 20, 1995 now U.S. Pat. No. 5,545,895.

FIELD OF THE INVENTION

The present invention relates to standardization of spectral data and the standardization of instrument bias or discrimination in spectral data.

BACKGROUND OF THE INVENTION

Mass spectrometry is an important tool for use in chemical analysis. One problem confronted in the field of mass spectrometry is that, over extended periods of time, mass spectrometers can experience sensitivity drift or mass discrimination drift, which is also referred to as instrument bias. Mass discrimination in a mass spectrometer may be described as the favorable or disfavorable transmission of ions of a particular mass-to-charge (m/z) relative to ions at other m/z values in the mass range of the instrument. In other words, mass discrimination drift describes mass dependent changes in transmission across the mass range of the instrument. Other analytical instruments experience similar instrument bias. In addition, the overall sensitivity of the analyzer may change independent of m/z, which may be attributed to a change in detector sensitivity. This shift is termed sensitivity drift.

In quantitative mass spectrometry, calibration of an instrument consists of constructing a quantitative model from standards that relates the response and concentrations of the individual components in a mixture to the spectral response of the mixture. Unfortunately, typical models constructed for quantitation do not perform well over extended periods of time without recalibrating the instrument to account for instrumental sensitivity drift or mass discrimination drift. Such instrument changes directly affect the relationship between the respective responses of the standards and their concentrations in the originally constructed model. Generally, these instrumental changes are corrected by generating a new calibration model that again relates the component response to concentration. For the analysis of multicomponent mixtures, total recalibration can be a costly and time-consuming process which removes the instrument from its intended application. Even for those cases where the instrument can be autocalibrated, other concerns frequently arise relating to cost, long term analyte stability, and the handling of potentially toxic analytical standards.

In addition to variations of transmission within a single instrument, another problem in chemical analysis is the variation in instrument bias among different instruments. Such variation can cause the spectrum of the same compound obtained on different instruments to differ substantially in appearance. This variation does not allow for the transfer of the previously mentioned quantitative models between instruments because the transmission and bias across the spectral range is unique to each individual instrument.

Library searching techniques are commonly employed to assist and expedite the identification of spectra from unknown compounds. Typical library searching techniques consist of matching or assimilating an unknown spectrum with entries in a spectral reference library. Compounds in the library that have similar spectra to the unknown can be tabulated according to a numerical similarity index generated by a search algorithm. The problem with these approaches is most spectral libraries are constructed using a variety of experimental conditions and instruments allowing for large differences between reference spectra for the same compounds. Using current searching techniques, the most reliable match of an unknown to an entry in the library is obtained by generating the unknown and the reference library spectra under as close to identical experimental conditions on the same instrument as possible. Such constraints are not always practical or feasible.

The practice of mass spectrometry would be improved by a method which reduces the time and costs associated with correcting for bias and sensitivity differences in spectral data. In addition, the practice of searching spectral libraries would be improved by a method which provides standardized spectral data which can be searched.

TERMS

In this specification, the term "biased" means the response of an instrument has changed beyond an application's defined tolerance level relative to the instrument's response at a time of reference, which may arbitrarily be designated as time, t=0. Thus, the term "biased" refers to relative instrument bias and does not necessarily represent absolute instrument bias. From the definition of "biased", the term "unbiased" as used in this specification does not imply having zero absolute bias, but instead, means having the same bias as or having actual bias very similar to the bias of standard reference spectra. Thus, an "unbiased spectrum" is a spectrum to which a transfer function has been applied to mathematically equalize bias or a spectrum which was obtained at the arbitrary reference time, t=0. Unbiased data may also be referred to herein as "standardized" data.

"Determination of the composition" of a sample refers to the identification of the components in a sample. This does not imply that the concentration of those components must also be determined, but such a determination is also possible.

The term "library" as used herein refers to a set of spectral data representative of the spectra of known compounds. The data in the library are preferably standardized to the same relative bias or a known relative bias.

The term "response channel" refers to a specific position along the x-axis of a spectrum wherein a spectrum is depicted as a graph with response (intensity) along the y-axis and a characteristic such as wavelength, m/z or time along the x-axis. For example, in mass spectrometry, a single m/z would correspond to a response channel.

The term "response factor" as used herein refers to the instrument's response to a given compound at a given response channel per unit concentration. Response factors can also be related to one another by normalizing to a given component; such normalized response factors are termed "relative response factors".

When reference is made to the "same time interval" in this specification, it means a time period during which the instrument bias of a working instrument does not change beyond an acceptable predetermined tolerance level for a given application. The "same time interval" can include time before and after an equivalent standard is run on the working instrument. In other words, an applicable transfer function may be obtained from the standardization step determined closest in time, either before or after, to the collection of the standardization spectra and the sample spectra to which a transfer function is to be applied.

The term "spectral data" refers to x,y data obtained from an instrument wherein the spectra may have "discrete peaks" or "broadened peaks". A spectrum may be characterized as having "discrete peaks" when the response (y-axis) of a peak at one response channel (x-axis) has no broadening mechanism, that is the response of a given response channel does not spread into adjacent response channels. For example, a mass spectrum of an analyte may give a response at one m/z and no response at an adjacent m/z. A spectrum may be characterized as having "broadened peaks" when the bandwidth of a single peak extends into adjacent response channels such that the response at one point along the x-axis is not confined to a single channel and, therefore, is also dependent on the response at an adjacent response channel. Examples of spectra having broadened peaks include spectra from instruments capable of infrared spectroscopy, fluorescence, ultraviolet-visible, and Raman.

The "spectral region of interest" refers to a region of the spectrum in which modeling of instrument bias is desired. This region is typically determined based on the region of the spectrum in which a sample of interest provides useful spectral information. The spectral region of interest can include a portion or portions of the sample spectral range, the entire sample spectral range, or a larger spectral range.

A "corresponding spectral region" refers to a region of a spectrum sufficiently covering the spectral region of interest with spectral information to permit modeling of instrument bias within the spectral region of interest. The "corresponding spectral region" of a surrogate standard is preferably between the response channel high and response channel low of a spectrum of a standard. The "corresponding spectral region" should provide adequate spectral information within the spectral region of interest, such that modeling of bias within the spectral region of interest is valid.

A "standard" may be composed of a single component which must not be influenced significantly by chemical impurities. A mixture may also be a standard if the components of the mixture can be reproduced in relationship to one another in terms of concentration. Components of a mixture are in a reproducible relationship to one another if they are in the same relative concentration ratio with respect to each other despite any potential additional components that may dilute their absolute concentrations. One restriction on potential additional components in a mixture used as a standard is that the spectrum of any additional component must not interfere with the spectrum of the components in the original mixture in a spectral region of interest which is to be corrected for instrument bias. If a dilution is made, the data would need to reflect the dilution factor to prevent the dilution from being interpreted as an overall change in instrument sensitivity.

Preferably, the standard comprises a known compound of a known concentration such that the information concerning the known concentration is retrievable; this information is useful to perform quantitation. Preferably, spectral data from the standard, such as peak intensity, from a spectral region of interest is known and retrievable in addition to the concentration so that a response factor may be determined for the standard.

The standard chosen to determine a transfer function may be termed either a "check-gas" or a "surrogate". When the standard is a "check-gas", the standard directly maps the bias at the individual response channels used in the sample spectrum's range of interest. Thus, the unbiased reference spectrum has peaks at every response channel as does the sample spectrum for the spectral region of interest. A standard may have additional peaks outside the range of interest that the sample does not have, but, under the check-gas approach, the standard must have at least a one-to-one match of peaks in the region of interest.

When the standard is a "surrogate", the standard comprises at least one component such that the surrogate standard gives a spectrum having adequate spectral information at response channels distributed throughout or beyond a spectral range of interest to allow the instrument bias to be modeled in said spectral range. The spectrum of the surrogate standard may have peaks at the same response channels as peaks from a spectrum of a sample; peaks from a surrogate standard can be positioned irrespective of the peak positions for the sample.

The term "equivalent standard" used herein refers to a component or a mixture of components that is equivalent in spectral information to a standard whose spectral data is retrievable over a spectral region of interest. Preferably, the standard and the equivalent standard are compositionally the same. In some cases, the only difference between the standard and the equivalent standard may be either the time at which each is run on a single instrument, or that each is run on a different instrument. Relative to the standard spectrum, the spectrum from the equivalent standard is a fingerprint of the change in bias of the working instrument, which is defined below.

The term "transfer function" mathematically describes the instrument bias of a working instrument in relation to an unbiased reference library of spectral data over a spectral region of interest. A transfer function may be a set of unique corrections for individual response channels or a function fitted to a set of response channels to transform spectral data to the same relative bias. A transfer function is applied to a biased spectrum at each response channel of interest in the biased spectrum. Thus, a transfer function corrects to a common bias rather than correcting for absolute instrument bias. In other words, applying a transfer function standardizes spectral data such that measurements may be made generally independent of instrument bias. Data to which a transfer function has been applied appear as if they were collected on the same instrument, during the same time interval, and under the same experimental conditions.

As used in this specification, a "working instrument" is an instrument on which the spectrum of a sample of interest is obtained. The working instrument can be identical to or different from the instrument from which the reference spectra are obtained. A "working instrument" is linked by a transfer function to data collected on a particular instrument with a set of unbiased reference spectra. In mass spectrometry a working instrument may be referred to as a working mass spectrometer.

A "working spectrum" is a spectrum obtained from the working instrument. The spectrum of an equivalent standard, acquired from the working instrument, will be referred to as a working spectrum. However, not all spectra acquired on the working instrument are necessarily termed "working spectra". For example, sample spectra acquired on a working instrument are working spectra, but they are more specifically termed "sample spectra".

SUMMARY OF THE INVENTION

One embodiment of the invention is a method useful, for example, for determining whether or not, and by how much the sensitivity or bias of an instrument may have drifted outside an acceptable, application defined tolerance level throughout a spectral region of interest. Generally, this method involves determining relative instrument bias by using spectra, of at least single standard, acquired at different times, or on different instruments. The observed changes in the spectra can be used to generate a mathematical function of the change in instrument bias.

The method of determining relative instrument bias from spectral data may be practiced, for example, for mass spectrometric data by the following steps. The first step is to acquire a reference spectrum which is representative of the mass spectrum of a standard. This initial reference spectrum will be referred to as an unbiased reference spectrum. Spectral information from this unbiased reference spectrum is preferably stored such that it is retrievable for future reference. A mass spectrum of an equivalent standard is acquired from a working mass spectrometer. Initially, this working spectrum of the equivalent standard is referred to as a biased working spectrum, because the instrument bias from the working instrument at the time the spectrum of the equivalent standard was obtained may differ from the instrument bias of the mass spectrometer from which, and at the time that, the reference spectrum was obtained. From the unbiased reference spectrum and the biased working spectrum, a transfer function can be derived to describe the relative bias which is represented in the biased spectrum. The transfer function comprises an expression which mathematically equates the biased working spectrum to the unbiased reference spectrum.

A transfer function may be determined not only from a set of mass spectra acquired from a single standard, but also from a set of mass spectrometric reference spectra acquired from a group of standards. The set of reference spectra should represent the mass spectrum of each standard in the group of standards, and as above, each spectrum in the set of reference spectra may be referred to as an unbiased reference spectrum which, preferably, is retrievable and stored. In the case of a group of standards, the equivalent standard used to generate a transfer function should be selected from the aforementioned group of standards that covers the spectral region of interest.

The transfer function obtained as described above may then be used to correct spectral data to account for the instrument changes. With this method, spectra from any number of standards will only need to be obtained once as long as their spectra fall within the region of interest of the standard. After the initial spectral data acquisition, any one standard may be used to represent the change in spectral response that all the other standards would likely experience within a corresponding mass range.

The reference spectrum of a standard and the working spectrum of an equivalent standard may be collected on separate instruments. One benefit of this approach is that the spectra collected on different instruments can be transformed to appear as if they were collected on the same instrument. Advantages of such standardization among instruments include easier sharing of data between laboratories and within laboratories equipped with multiple instruments.

Alternatively, the working spectrum of an equivalent standard and the reference spectrum of a standard may be collected on the same instrument, referred to as the working instrument. If collected on the same instrument, then spectral data obtained from the same instrument at different times may be transformed to appear as if it were obtained under similar experimental conditions. One benefit of this approach would be to measure or account for drift in the same instrument over time.

The method of the present invention is also useful for data comparison or library searching of spectral data because the present method may be used to transform spectral data to appear as if the same instrument obtained each spectrum under similar experimental conditions. This may be achieved, for example, by acquiring a biased sample spectrum of a sample on a working instrument, wherein the sample has an equivalent in the spectral reference data set. This biased sample spectrum should be obtained during the same time interval that the spectrum was acquired from an equivalent standard on the working instrument; the instrument from which the reference spectrum of the standard was obtained need not be the working instrument. The transfer function, generated using data from the equivalent standard as discussed above, may then be applied to each said biased sample spectrum of similar spectral range to that of the equivalent standard to obtain an unbiased sample spectrum within the spectral region of interest. Any number of biased sample spectra may be converted using a transfer function obtained as described above. These spectra may then be stored to create a library of spectral data which is standardized to the same bias.

The invention provides an improved method of library searching to qualitatively identify unknown compounds. To identify the composition of a sample giving rise to a sample spectrum, an unbiased spectrum of the sample can be used to search the unbiased reference spectra for a match. Because the sample spectrum and the reference spectra stored for standards are transformed to the same bias, the similarity between a reference spectrum for a standard and a sample spectrum for a sample containing that standard will be enhanced. Therefore, the quality of the search results (matches) will be improved which is the goal of library searching.

In addition to enhancing qualitative identification of a sample, the invention can be used to enhance the quantitative determination of components analyzed, for example, by mass spectrometry. By correcting for changes in mass discrimination or bias over time in the same mass spectrometer, the present invention simplifies on-line quantitation. This may be achieved by modeling the information from at least a portion of the unbiased sample spectrum with information from a corresponding region of an unbiased reference spectrum of a standard containing the component of interest. For quantitative measurements, the standard should comprise a known compound of a known concentration such that the amount of said known concentration is retrievable. Also, using the above method for quantitation, regenerating all components comprising a multicomponent model and performing a total recalibration with a set of standards each time a mass spectrometer drifts is unnecessary.

DETAILED DESCRIPTION OF THE INVENTION

Figure 1:
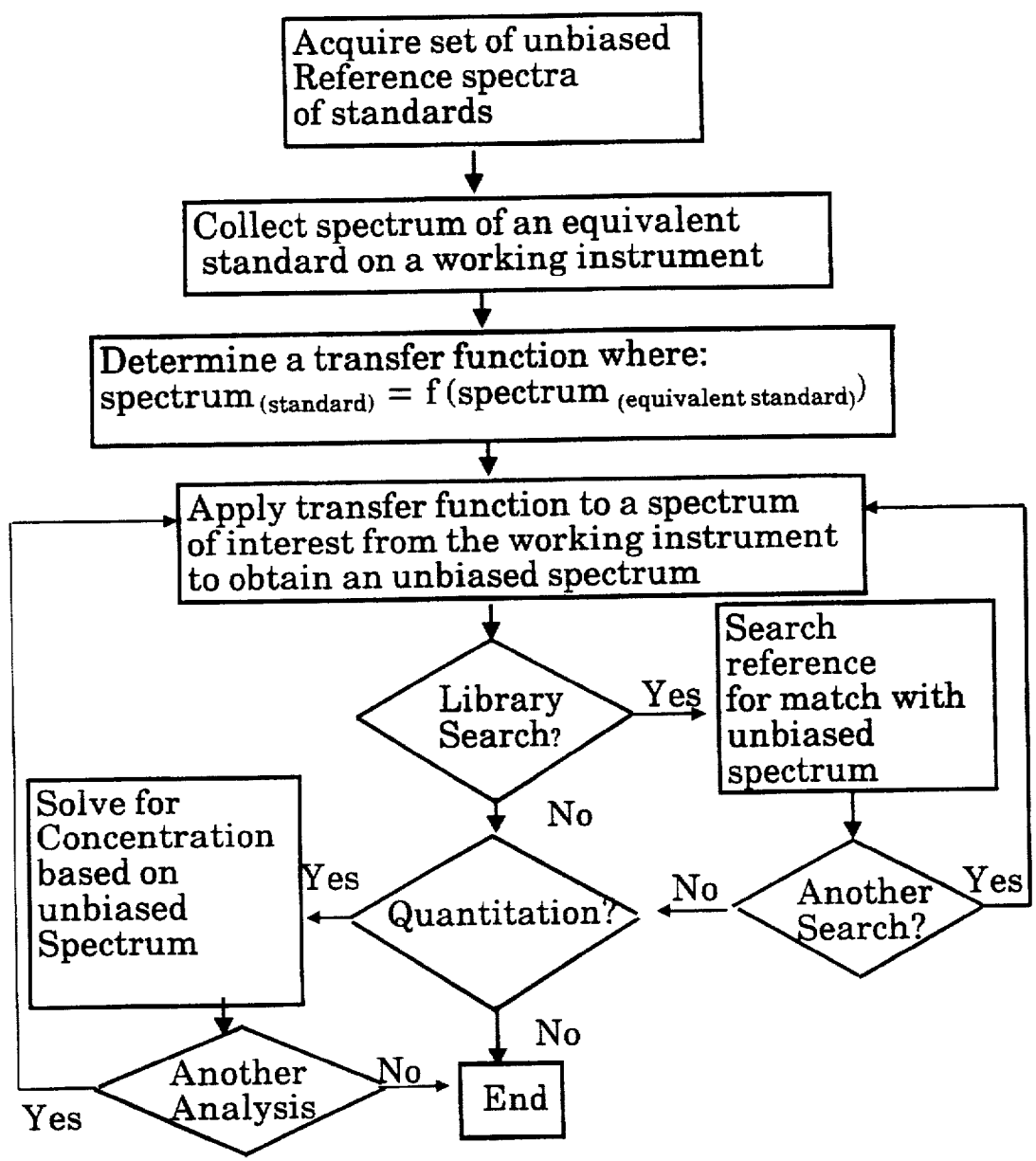
FIG. 1 is a flow chart incorporating different embodiments of the process of the present invention.

Referring now to FIG. 1, first a set of unbiased reference spectra of standards is acquired from pure components or from mixtures. A reference spectrum is a spectrum which represents the spectrum of a standard. A reference spectrum may be acquired by several means such as from a textbook, by running a sample on an instrument, or by artificial generation. If stored, data from a reference spectrum should be stored in an unbiased form. Preferably, such reference spectra are stored and retrievable in a common library for ease of comparison with sample spectra. For quantitation of a component of interest in a sample, the component of interest should be represented by an unbiased reference spectrum which is in the library and is of known concentration.

The second step depicted in FIG. 1 is to collect a spectrum on a working instrument of an equivalent standard. The equivalent standard is equivalent to a standard whose spectrum was acquired in the first step in FIG. 1 over the spectral region of interest.

From the spectra obtained in the aforementioned steps, a transfer function can be determined wherein the unbiased reference spectrum of a standard is related by a function to the biased spectrum of an equivalent standard taken on a working instrument. This relationship may be represented mathematically as:

$$\text{UNBIASED SPECTRUM}_{standard} = f(\text{BIASED SPECTRUM}_{equivalent\ standard})$$

Note that the reciprocal mathematical relationship also holds. Preferably, a computer is used to derive the transfer function, however, simple derivations may be done by hand. If a computer is used to derive the transfer function, the transfer function need not be displayed; for example, the transfer function may be entered directly into a data file.

The transfer function may be applied to data of interest to equalize instrument bias between the working spectra and the reference spectra; thus, a transfer function links a spectrum of a standard with that of an equivalent standard. When multiple unbiased reference spectra are available, any standard whose reference spectrum is retrievable and representative of a spectral region of interest may be used as an equivalent standard to determine a transfer function for the spectral region of interest.

An advantage to using this standardization method is that a single standard may be used to obtain a transfer function and to standardize several spectra over a spectral region of interest. Preferably, the transfer function that is obtained is updated as needed. Thus, the transfer function may be determined repeatedly at periodic or varied time intervals to compensate for relative instrument bias that results over time in a mass spectrometer over a spectral region of interest. Within any specific time interval, instrument bias may be standardized by applying a transfer function valid for that time interval.

The rationale behind updating of the transfer function is that the time the sample of interest is acquired should be within a time where the instrument bias does not change beyond some application defined tolerance level in order for the data to be considered unbiased after the transfer function is applied. A new transfer function is preferred when the transfer function changes beyond the acceptable tolerance for at least one response channel of interest. A tolerance should be built into applications of prolonged data acquisition to determine when an update of the transfer function is necessary because the spectral response may not change significantly for days or months.

As discussed above, standardizing bias from any number of spectra obtained within the same time frame may be done using the same transfer function by applying the appropriate transfer function over the spectral range of interest. Once the transfer function is updated, a new transfer function is obtained which can replace the previous transfer function or can be stored along with any previous transfer functions to serve as a diagnostic history for a particular working instrument.

To create a library of standardized spectral data, an unbiased reference spectrum of an additional standard may be stored as follows. A biased spectrum of the standard to be added to the reference set of spectra is acquired during the same time interval as the acquisition of a spectrum of an equivalent standard which is equivalent to a standard already available for reference. A transfer function is generated using the biased spectrum of the equivalent standard within a similar spectral range as the spectrum of the reference standard to which it is equivalent. The transfer function is applied, over a corresponding spectral region, to the biased spectrum of the additional standard, to obtain an unbiased reference spectrum of the additional standard. Finally, at least a portion of the unbiased reference spectrum of the additional standard should be stored such that it is retrievable for future use.

The spectrum of a sample for analysis is referred to as a sample spectrum. The sample is ideally related to standards whose data are stored in the library of standards. More specifically, the sample preferably contains at least one component whose representative spectrum is retrievable for comparison. Note that a sample may be a standard from which future transfer functions may be determined, once spectral data is unbiased. The sample may be introduced into an instrument in any conventional manner, for example, by injection of a small aliquot into the batch inlet of a mass spectrometer. A sample spectrum should be obtained on the working instrument and during the same time interval that the spectrum of an equivalent standard was obtained. Thus, a transfer function determined as described above may be applied to transform the sample spectrum to an unbiased sample spectrum as referred to in the fourth box in FIG. 1.

Referring to the decision boxes of FIG. 1, the transfer function may be applied to enhance a library search, to do quantitation, to do both or to do neither. If a library search is to be implemented, a computer can compare information from an unbiased spectrum of interest with a set of the unbiased reference spectra to search for a match. It is understood when searching spectral data that the term "match" does not necessarily refer to identical spectra but can refer to the best fit for the data available. Matching spectra generally meet a predefined similarity index based on the search algorithm used. If quantitation is to be implemented, a computer can solve for concentration based on comparing the unbiased sample spectrum from the working instrument with the unbiased spectra from standards of known concentration that comprise the sample. If both quantitation and library searching are to be performed using the same spectrum, the library search should be performed first to identify the components comprising the sample.

The composition of the sample may be determined by searching the stored unbiased reference spectra for a match with the unbiased sample spectrum. Searching may be implemented using a commercial library search algorithm as is commonly available as part of the data systems for these instruments. For a discussion of mass spectral library search algorithms, see, for example, Stein, S. E.; Scott, D. R. *J. Am. Soc. Mass Spectrom.* 1994, 5, 859–866. Assuming that spectral information from the components in the sample are in the library, an extension of the current practice in library searching capabilities would be the capability to perform quantitation directly from library entries, if the library entries included data on analyte response factors. The capability to standardize instrumental bias before a library search should permit quantitation, as well as the identification of unknowns, directly from the library. Using the transformed and unbiased sample spectrum and the unbiased spectral reference data in the library it should be possible to: (i) search the library to identify the component(s) in the spectrum, (ii) account for multiple components in the spectrum, (iii) maintain and augment the library, and (iv) quantitate without the need to recalibrate the instrument for the components in the sample of interest. The impact would be greatest in the identification and quantitation of unknowns in samples where standards corresponding to the unknowns were stored as unbiased reference spectra.

Enhanced library searching may be implemented by generating a library of unbiased spectral data wherein the spectral data is unbiased relative to other library entries over corresponding spectral regions. A sample spectrum, that is representative of instrumental bias for a working instrument, may be obtained on that working instrument. A transfer function is determined, as previously discussed, to link the sample spectrum and the set of reference library data to account for bias in the sample spectrum. The unknown sample spectrum collected on the working instrument may then be transformed such that relative instrument bias is removed from the spectrum. With the present method, multiple instruments could be used to generate a single 'standardized' library which could be used on any instrument by transforming data obtained on the respective instrument to be consistent with the unbiased library data.

Although the standardization method described herein is discussed with specific reference to mass spectrometry, libraries of standardized spectral data may also be acquired and searched in other analytical applications, for example, where spectral data is obtained on instruments capable of spectroscopic measurements. The method of standardization selected is preferably based on the type of spectral data obtained for a particular analytical application. Spectra may be characterized generally as comprising discrete peaks or broadened peaks with respect to response channels along the x-axis. (See the definitions under "spectral data" in the terms section.)

Standardization of spectral data to a common bias is amenable to the standardization approach described herein for those instruments, such as mass spectrometers, sensor arrays, or filter photometers, which give rise to spectra having discrete peaks. In brief, this standardization approach standardizes the bias in the spectral responses of two sets of spectral data by applying a transfer function across the spectral region of interest wherein the transfer function may be obtained using spectra from a single standard common to both sets of data. When applying this method, the positions of peaks on the response channels should remain constant to allow spectral y-response changes to be adequately modeled.

For applications giving rise to spectra having broadened peaks, in other words, which have adjacent response channels with related spectral data, mathematical techniques such as piecewise direct standardization may be preferable. Piecewise direct standardization can correct for shifts in both intensity and response channel even though both x and y corrections are not a prerequisite for the technique.

In piecewise direct standardization, the spectra obtained from a set of standards and from a set of equivalent standards may be related by the equation $$\overline{R}_1 = \overline{R}_2 F$$

where $\overline{R}_1$ is a set of unbiased spectra of standards, $\overline{R}_2$ is a set of biased spectra of equivalent standards, and F is a transformation matrix or a transfer function. Spectra from more than one standard/equivalent standard pair should be employed to obtain a transfer function for spectra having broadened peaks in order to permit correction for changes in both the x and y directions. In most optical applications, the response (intensity) is continuous with respect to response channels because of the bandwidth of the spectral features represented by the data. Correcting for spectral changes in both the x and y dimension results in the transfer function F being a banded diagonal matrix of the form $$F = \text{diag}(b_1^T, b_2^T, \ldots b_i^T, \ldots b_p^T)$$

where $b_i$ is a vector of transformation coefficients for the i-th response channel and p is the total number of response channels included. The number of elements in $b_i$ equals the window size used for piecewise direct standardization, which can be determined, for example, using a cross-validation procedure as is known in the art. In cross-validation, F matrices of varying window sizes are constructed and evaluated for performance. Once the transfer function F is determined, any response from a sample measurement on an instrument, $r_{2,un}$, can be standardized to the set of stored library spectra to appear as if it were generated on an instrument with bias equivalent to that used to create library spectra based on the following equation:

$$r_{1,un}^T = r_{2,un}^T F,$$

where $r_{1,un}^T$ is the unknown spectrum after standardization, i.e., how $r_2^T$, would appear if run on instrument 1 For further discussion on standardizing spectral data using spectra having broadened peaks by PDS, see for example, U.S. Pat. No. 5,459, 677 to Kowalski which is herein incorporated by reference; Wang et al., Multivariate Instrument Standardization, Anal. Chem, 64, 1991, 2750–2756; or Wang et al., Improvement of Multivariate Calibration through Instrument Standardization, Anal. Chem. 64, 1992, 562–564. Before standardization, spectral data having broadened peaks are preferably smoothed to minimize random noise using common spectral smoothing techniques. Similarly, smoothing of the transformation function may also be applied to improve the performance of the technique.

Turning now to quantitation, after an initial calibration model for quantitation is developed, which will be described below, the concentration of multiple components in a sample may be determined as follows. The transfer function may be applied to the reference spectra to make the reference spectra appear as if they have the same relative bias as the sample spectrum. Then, the contribution of each reference spectrum to the sample spectrum is determined from the transformed reference spectra of those components. (Note that the transfer function could also be applied to the sample spectrum to obtain an unbiased sample spectrum which can be compared to the unbiased reference spectra. As long as the sample spectrum and the reference spectra are transformed to the same relative bias this method is valid.) The contribution of each component of interest is related to an unbiased reference spectrum representative of each component of interest. The entire spectrum need not be compared if the needed information is within a narrower region of interest. When determining the concentration for multiple components, a computer program may be used to account for potential overlap in the spectra.

Quantitative analysis typically involves an approach where a set of standards or mixtures of known concentration are analyzed to determine the manner in which an analyte's concentration affects the instrument's response. The following describes calibration of a mass spectrometer and similar calibration approaches would be amenable to other spectroscopy techniques. In mass spectrometry, initial calibration of a mass spectrometer for quantitative analysis of multiple analytes in a mixture using regression analysis generally comprises two parts. First, representative mass spectra for all analytes that comprise the mixture should be determined; and second, the response factors for each respective analyte in the mixture should be determined. Since the peak heights of various ions in a mass spectrum for a given compound are proportional to the partial pressure (concentration) of that compound, and since Dalton's law of partial pressures applies, the peak heights for different components in the mixture are quantitatively additive. For a multiple component sample, regression methods such as least squares allow the contribution of the individual components in the mass spectrum of the mixture to be determined from a set of spectra of the pure analytes. The type of regression technique is not critical, as long as the technique relates the response of the mixture to the response of the components which comprise the mixture and whose concentration are known.

For a single component sample, initial calibration requires similar steps as initial calibration of a multiple analyte sample, except the need to account for potential overlap from other analytes is eliminated. After a sample spectrum has had a transfer function applied such that the sample spectrum is unbiased relative to reference spectra of interest, concentration of the analyte comprising the sample may be determined. For a single component sample, such a determination is implemented by relating a spectral intensity at a given m/z of interest of the unbiased sample spectrum to a corresponding m/z of an unbiased reference spectrum of known concentration containing the component of interest. The term 'relate' can mean determining concentration of a sample by the quotient of the response of a sample to a response factor from a stored standard for the analyte in the sample. The invention may also be used to update response factors to account for sensitivity drift. Such response factors are useful for quantitation because the instrumental response for response factors is influenced by sensitivity drift or instrument bias.

A single mass spectrometer may be configured such that more than one detector could be used at different m/z's. If more than one detector is used, the bias of each detector should be accounted for in addition to instrument bias associated with the transmission of the mass spectrometer. Using the check-gas approach as will be described in Example 1, the varied sensitivity among detectors at different masses may be mathematically modeled since the check-gas approach maps the change at each discrete m/z detector.

Transforming a spectrum for relative instrument bias provides a means of standardization of mass spectrometric data. To summarize the standardization process, mass spectrometric data can be standardized by the following steps. The transformation process begins through the acquisition of a set of mass spectrometric reference spectra from a group of standards. This set of reference spectra is representative of the mass spectra of each standard in the group of standards. Each individual spectrum in the set of reference spectra is referred to as an unbiased reference spectrum, and these unbiased reference spectra should be stored and retrievable.

A biased mass spectrometric working spectrum of an equivalent standard on a working mass spectrometer is acquired, and, during the same time interval, a biased sample spectrum of a sample is acquired on the working mass spectrometer. A transfer function is then applied to the biased sample spectrum to obtain an unbiased sample spectrum. The transfer function represents the relationship between the unbiased reference spectrum and the biased working spectrum, and may be mathematically derived, for example, by a computer.

The concentration of components of interest in a sample may be determined by identifying the corresponding stored and unbiased reference spectra, which are identified by the user or through a library search, and determining the concentration of the components in the sample by relating the unbiased sample spectrum with the unbiased reference spectra for those components identified to comprise the standard.

As mentioned, the reciprocal relationship, relating the unbiased sample spectrum to the unbiased reference spectra, is equally valid to the standardization of mass spectrometric data.

EXAMPLE 1

The following example demonstrates a method of correcting for mass discrimination for a mass spectrometer wherein the standardization method is applied to the quantitative analysis of a multicomponent mixture. The method uses a check-gas to correct the intensity of each m/z directly by using the mass spectrum from a standard that is measured at the time the calibration model is constructed and using a second mass spectrum from an equivalent standard at a later time after change in bias has affected the instrumental response. These spectra determine the transformation that is required to correct the reference data in the calibration model for the change in bias that affected instrumental response.

When using a check-gas, the method to determine the transfer function or transmission correction matrix F is simplified in that a mathematical fitting of the spectral data is not required to determine the transmission correction for m/z values not modeled by the standard.

Authentic spectra were generated from reagent grade solvents of ethylene dichloride, methylene chloride, vinylidene chloride, and n-heptane as obtained from a commercial supplier. Percentage level liquid standards of the solvents were prepared by weight as mixtures to use as test standards for this example. When the term 'mixture 1' is used in these examples, it refers to a mixture of 41.1% methylene chloride, 28.4% vinylidene chloride, 30.5% ethylene dichloride by weight. Similarly, 'mixture 2' refers to a mixture of 53.9% methylene chloride, 18.7% vinylidene chloride, 27.7% ethylene dichloride by weight.

In quantitative mass spectrometry, for a given concentration $C_n$ of the nth component in the ionization chamber, there will be an intensity of ion current; for a given ion, the intensity $M_{mn}$ is directly related to the concentration given by equation (1).

$$M_{mn} = R_m S_n C_n \qquad (1)$$

Here the subscript m refers to an ion of m/z value m, and the subscript n refers to an analyte n. $R_m$ is the relative abundance of the mth ion in the mass spectrum of the pure analyte n, and $S_n$ is the response factor giving rise to $M_{mn}$ for the pure component for the mth ion of known concentration. Equation (1) assumes that for a given mass spectrometer and for given ion source conditions, the relative intensities of the various ions, $R_m$, are constant in the mass spectrum for a given period. However, sensitivity drift and mass dependent transmission changes of the mass spectrometer often vary over time. Thus, a recalibration of the instrument is required to correct the $R_m$ and $S_n$ terms in equation (1). Other quantitative models which relate the mass spectrometric response to analyte concentration such as those that combine the $R_m$ and $S_n$ terms into a single term are also valid in this discussion.

Standardization, as used in this method, assumes that the transmission of ions of different m/z across the measured mass range are compound independent but mass dependent and detector dependent. With this assumption, the relative abundance of the mth ion in the mass spectrum, $M_{mn}$, can be corrected for mass discrimination or instrument bias with a mass dependent transmission correction factor, $F_m$, representative of the value of a transfer function at mass m. As used here, $F_m$ may correct for both an offset and slope dependency between the biased and unbiased data sets. $F_m$ as used in this example weights the initial response, $R_m$, recorded at the time of the initial calibration by the observed change in transmission for the mth ion for the pure analyte as shown in equation (2). Thus, instrumental changes in transmission are not erroneously attributed to analytical changes in concentration, $C_n$. The reciprocal relationship could similarly be applied to the intensity $M_{mn}$; this correction would have the same effect on $C_n$ and would have the affect of correcting the current instrumental response to appear as if data were acquired at the same time as $R_m$.

$$M_{mn} = F_m R_m S_n C_n \quad (2)$$

In a multicomponent mixture, typically the spectra from one or more of the peaks from different components in the mixture overlap with each other. In other words, it is highly unlikely that every component in the mixture will have a unique mass spectral peak in the mass spectrum of the mixture. Spectral overlaps in the spectra of multicomponent mixtures can be accounted for by using a set of linear equations to describe the contributions of the individual components in the mixture to the mass spectrum such as that given by equation (3). Equation (3) as written supports the fundamental assumption that the sensitivity change for a mass spectrometer is compound independent but mass and detector dependent.

$$
\begin{aligned}
M_1 &= F_1 R_{11} S_1 C_1 + F_1 R_{12} S_2 C_2 + \ldots + F_1 R_{1n} S_n C_n \\
M_2 &= F_2 R_{21} S_1 C_1 + F_2 R_{22} S_2 C_2 + \ldots + F_2 R_{2n} S_n C_n \\
\ldots &= \ldots + \ldots + \ldots + \ldots \\
M_m &= F_m R_{m1} S_1 C_1 + F_m R_{m2} S_2 C_2 + \ldots + F_m R_{mn} S_n C_n
\end{aligned}
\quad (3)
$$

wherein $M_m$=the sum of individual responses of each component of interest in the spectrum at m/z m;

$F_m$=the transmission correction factor or the value of a transfer function at m/z m;

$R_{mn}$=the relative abundance of an ion at m/z m in the mass spectrum of the standard containing analyte n;

$S_n$=response factor for component n that accounts for the response of component n at a known concentration;

$C_n$=concentration of component n in the mixture. In the aforementioned equation, the $R_{mn}$ and $S_n$ terms may also be combined into a single term. The linear equations given by equation (3) can be rewritten in matrix notation as shown in equations (4) and (5). In the matrix notation given by equation (5), F is the transfer correction in matrix form, and R is the reference component matrix representing data from pure analytes, or standards as this term is defined above, that comprise the mixture. S is the response factor matrix; C is the concentration coefficient matrix; and M is the mixture response matrix. The transfer matrix as shown only has non-zero values along the diagonal of the matrix since a given correction value corrects the intensity of a given m/z described in the calibration model. This is only one embodiment of the invention. For example, an equally valid approach could include non-zero off-diagonal values in the matrix if a correction in the m/z scale was also required by the model.

$$
\begin{bmatrix} F_1 & 0 & 0 & 0 \\ 0 & F_2 & 0 & 0 \\ 0 & 0 & F_{\ldots} & 0 \\ 0 & 0 & 0 & F_m \end{bmatrix}
\begin{bmatrix} R_{11} & R_{12} & \ldots & R_{1n} \\ R_{21} & R_{22} & \ldots & R_{2n} \\ \ldots & \ldots & \ldots & \ldots \\ R_{m1} & R_{m2} & \ldots & R_{mn} \end{bmatrix}
\begin{bmatrix} S_1 & 0 & 0 & 0 \\ 0 & S_2 & 0 & 0 \\ 0 & 0 & S_{\ldots} & 0 \\ 0 & 0 & 0 & S_n \end{bmatrix}
\begin{bmatrix} C_1 \\ C_2 \\ C_{\ldots} \\ C_n \end{bmatrix}
=
\begin{bmatrix} M_1 \\ M_2 \\ M_{\ldots} \\ M_m \end{bmatrix}
\quad (4)
$$

$$FRSC = M \quad (5)$$

Using matrix notation, the solution for the concentration coefficient matrix, C, can be written as shown in equation (6).

$$C = S^{-1}(R^T R)^{-1} R^T F^{-1} M \quad (6)$$

Normalization of the concentration coefficients, $C_n$, removes imprecision in the data associated with changes in the total sample pressure in the ion source or changes in overall sensitivity from one data set to another. Normalization as used here is defined as a percentage of the sum of all the concentration coefficients in C as shown in equation (7). In equation (7), %Nn is the concentration of component n in the multicomponent mixture.

$$\% N_n = 100 \left( C / \sum_{i=1}^{n} C_i \right) \quad (7)$$

The use of the transmission correction terms in equations (2) through (6) forms the basis for the application of standardization to quantitative mass spectrometry. The approach would have similar applicability in the previously discussed model that combines the R and the S matrix into a single term R' to form a new model, i.e., FR'C=M would be applicable to standardization as described herein.

The quantitative model using standardization was constructed using a mixture of methylene chloride (MC), vinylidene chloride (VDC), and ethylene dichloride (EDC). The data used in constructing and evaluating the model is given below in Table 1. In the development of a quantitative model, the preferred route of development would be to construct the R and M matrices, followed by the S matrix, and then the F matrix. The F matrix should be equivalent to the identity matrix, I, at the time the model is constructed. After the model is constructed, components having unbiased spectral data in the library may be added to the model and the current F matrix may be used.

The reference component and mixture response matrices, R and M, used in this model were formed by acquiring mass spectra from the pure components of the mixture and from mixtures of methylene chloride, vinylidene chloride (VDC), and ethylene dichloride (EDC).

used in equation (10). Equation (9) can then be rewritten as equation (11).

$$\% N_{corr_n} = 100 \left( \frac{C_n'}{S_n} / \sum_{i=1}^{n} \frac{C_i'}{S_i} \right) \quad (11)$$

Taking the ratio of the incorrect estimate, $\%Nincorr_n$, to the correct estimate, $\%N_{corr_n}$, gives K which is represented by equation (12). $\%N_{corr_n}$ represents the actual concentration of component n in the standard and is determined during sample preparation.

$$\frac{\% N_{incorr_n}}{\% N_{corr_n}} = K = \left( \left( \frac{S_n}{S_n'} \right) \left( \frac{\sum_{i=1}^{n} \frac{C_i'}{S_i'}}{\sum_{i=1}^{n} \frac{C_i'}{S_i}} \right) \right) \quad (12)$$

$$\begin{bmatrix} F_{49} & 0 & 0 & 0 & 0 & 0 & 0 & 0 & 0 & 0 & 0 \\ 0 & F_{51} & 0 & 0 & 0 & 0 & 0 & 0 & 0 & 0 & 0 \\ 0 & 0 & F_{61} & 0 & 0 & 0 & 0 & 0 & 0 & 0 & 0 \\ 0 & 0 & 0 & F_{63} & 0 & 0 & 0 & 0 & 0 & 0 & 0 \\ 0 & 0 & 0 & 0 & F_{84} & 0 & 0 & 0 & 0 & 0 & 0 \\ 0 & 0 & 0 & 0 & 0 & F_{86} & 0 & 0 & 0 & 0 & 0 \\ 0 & 0 & 0 & 0 & 0 & 0 & F_{88} & 0 & 0 & 0 & 0 \\ 0 & 0 & 0 & 0 & 0 & 0 & 0 & F_{96} & 0 & 0 & 0 \\ 0 & 0 & 0 & 0 & 0 & 0 & 0 & 0 & F_{98} & 0 & 0 \\ 0 & 0 & 0 & 0 & 0 & 0 & 0 & 0 & 0 & F_{100} & 0 \\ 0 & 0 & 0 & 0 & 0 & 0 & 0 & 0 & 0 & 0 & F_{102} \end{bmatrix} \begin{bmatrix} R_{49MC} & R_{49VDC} & R_{49EDC} \\ R_{51MC} & R_{51VDC} & R_{51EDC} \\ R_{61MC} & R_{61VDC} & R_{61EDC} \\ R_{63MC} & R_{63VDC} & R_{63EDC} \\ R_{84MC} & R_{84VDC} & R_{84EDC} \\ R_{86MC} & R_{86VDC} & R_{86EDC} \\ R_{88MC} & R_{88VDC} & R_{88EDC} \\ R_{96MC} & R_{96VDC} & R_{96EDC} \\ R_{98MC} & R_{98VDC} & R_{98EDC} \\ R_{100MC} & R_{100VDC} & R_{100EDC} \\ R_{102MC} & R_{102VDC} & R_{102EDC} \end{bmatrix} \begin{bmatrix} S_{MC} & 0 & 0 \\ 0 & S_{VDC} & 0 \\ 0 & 0 & S_{EDC} \end{bmatrix} \begin{bmatrix} C_1 \\ C_2 \\ C_3 \end{bmatrix} = \begin{bmatrix} M_{49} \\ M_{51} \\ M_{61} \\ M_{63} \\ M_{84} \\ M_{86} \\ M_{88} \\ M_{96} \\ M_{98} \\ M_{100} \\ M_{102} \end{bmatrix}$$

The S matrix, was determined for the model by the following method. In equation (6), consider the product of the diagonal matrix $S^{-1}$ (inverse response factor matrix) with the $(R^T R)^{-1} R^T F^{-1} M$ matrix as a correction that adjusts the concentration coefficients such that the response given by the mass spectrometer predicts the correct concentration in the mixture. In other words, $$C_{corr} = S^{-1}(R^T R)^{-1} R^T F^{-1} M = S^{-1} C_{incorr} \quad (8)$$

where the product $S^{-1}C_{incorr}$ represents the correction made to the concentration coefficients to give $C_{corr}$.

Separating the response factor terms from the concentration coefficient terms in equation (8) allows equation (7) to be rewritten as equation (9).

$$\% N_n = 100 \left( \frac{C_n}{S_n} / \sum_{i=1}^{n} \frac{C_i}{S_i} \right) \quad (9)$$

Now referring to equation (9), assume that the response factor for the nth component has response factors $S'n$ and concentration coefficients $C'n$ that are incorrect. Applying these restrictions to equation (9) gives rise to an incorrect concentration estimate for component n, $\%N_{incorr_n}$, as defined in equation (10).

$$\% N_{incorr_n} = 100 \left( \frac{C_n'}{S_n'} / \sum_{i=1}^{n} \frac{C_i'}{S_i'} \right) \quad (10)$$

Now also let equation (9) represent a correct concentration estimate for nth component, $\%N_{corr_n}$; this implies that the nth component will also have a correct response factor $S_n$ and the same incorrect concentration coefficient $C'_n$ as that The normalization terms (i.e., the summation terms) in equation (12) can be ignored since these terms serve as scaling factors for all components in both estimates. The normalization term in effect relates the response factors to each other and thereby redefines the response factors as relative response factors. Ignoring the normalization term, equation (12) simplifies to equation (13).

$$\frac{\% N_{incorr_n}}{\% N_{corr_n}} = K = \left( \frac{S_n}{S_n'} \right) \quad (13)$$

Solving for the correct $S_n$ term in equation (13) gives equation (14).

$$S_n = \left( \frac{\% N_{incorr_n}}{\% N_{corr_n}} \right) S_n' = KS_n' \quad (14)$$

The method for determining response factors for a quantitative model is easily implemented and simplified by assuming that all components in a mixture or mixtures of known composition have the same $S'_n$ value, before the composition of the standard is predicted by the regression model, i.e., assume S equals the identity matrix I. With the assumptions that both the S and F matrices equal I at the time the quantitative model is constructed, the solution for the regression model given by equation (6) simplifies to equation (15). Equation (15) is used along with equation (10) to determine $\%Nincorr_n$. Then $(\%N_{incorr_n}/\%Ncorr_n)$ equals Sn for component n in the mixture.

Using the R matrix and the unbiased response matrices M from mixtures 1 and 2 (shown in Table 1) as calibration standards, the $\%N_{incorr_n}$ and $S_n$ values for the respective analytes (shown in Table 2) were determined accordingly. In this example, the average of the response factors determined from mixtures 1 and 2 were used to generate the response factor matrix S.

$$C = (R^T R)^{-1} R^T M \quad (15)$$

S corrects for a component's response related to concentration in the mass spectrometer. When S is determined as above, S need only be determined once. After the initial determination of the S matrix, the F matrix as described herein may be used, to account for sensitivity drift or instrument bias.

Returning now to the discussion using standardization. Table 3 shows the concentration results predicted by the model using classical least squares with the revised regression model and configured with the R and S matrix parameters (Table 1) and the F matrix set equal to the identity matrix, I, for the mass spectrometer in both the "unbiased" and in the "biased" modes for the two test mixtures. As shown by the concentration estimates in Table 3, the estimates are accurate and precise when the calibration holds. In fact, the precision of the model for the "unbiased" response has less than 2% relative error. The data in the table also shows the errors that arise in the concentration estimates when a shift in mass transmission occurs within the instrument without a correction being made to the calibration model.

If the components that comprise the check-gas standard are stable and have m/z's that map the intensities for all m/z's used in the model, the method to determine the transmission correction matrix F is simplified in that it is possible to measure only the change in transmission for the m/z values being used in the model by simply applying equation (16).

$$F_m = (M_m(STD)\text{biased}/M_m(STD)\text{unbiased}) \quad (16)$$

Table 4 shows the mass dependent correction factors from a check-gas containing MC, VDC, and EDC that were determined from spectra acquired at the time the quantitative model was constructed to give an unbiased spectrum and at a later time when the instrument exhibited relative bias. The responses at the m/z's used in the calibration model taken from the biased and unbiased spectra were used to generate the bias corrections shown in Table 4 by applying equation (16). Using these correction factors for the F matrix in the regression model, the normalized concentration estimates for the biased mixture spectra from mixtures 1 and 2, shown in Table 5, were within 2% relative error to that measured for the standard. The 2% relative error seen in the estimates for this method is within the relative error of the model itself at the time the model was developed (i.e., F equal to I).

Errors associated with collecting the data at different amplifier gain ranges with similar sampling parameters can result in differences in the signal-to-noise for the different m/z values. The use of low level ions in determining the transformed values should be minimized in all quantitative models unless uniform signal-to-noise can be guaranteed for all amplifier gain ranges used in the measurements.

TABLE 1

$R_{mn}$ and $M_m$ Multivariate Regression Model Values

| | $R_{mn}$ Values | | | $M_m$ Unbiased Values | | $M_m$ Biased Values | |
|---|---|---|---|---|---|---|---|
| m/z (m) | Methylene Chloride | Vinylidene Chloride | Ethylene Dichloride | Mixture 1 | Mixture 2 | Mixture 1 | Mixture 2 |
| 49 | 100.0 | 3.3 | 100.0 | 100.0 | 100.0 | 100.0 | 100.0 |
| 51 | 29.1 | 1.5 | 32.8 | 30.7 | 30.1 | 31.4 | 30.9 |
| 61 | 0.0 | 100.0 | 41.2 | 80.6 | 42.5 | 89.0 | 47.4 |
| 63 | 0.0 | 30.7 | 50.9 | 31.4 | 18.3 | 35.3 | 20.2 |
| 84 | 81.2 | 0.0 | 0.0 | 65.9 | 70.9 | 90.5 | 96.0 |
| 86 | 50.9 | 0.0 | 0.0 | 41.2 | 44.3 | 57.4 | 61.2 |
| 88 | 7.5 | 0.0 | 0.0 | 6.4 | 6.8 | 8.6 | 9.0 |
| 96 | 0.0 | 60.2 | 4.3 | 45.2 | 23.3 | 68.0 | 35.0 |
| 98 | 0.0 | 37.7 | 40.9 | 35.1 | 19.8 | 54.2 | 30.2 |
| 100 | 0.0 | 5.7 | 24.6 | 8.5 | 5.4 | 13.0 | 8.1 |
| 102 | 0.0 | 0.0 | 4.0 | 0.8 | 0.6 | 1.0 | 0.8 |

TABLE 2

Response Factor Determination

| | % $N_{com}$ (Standards) | | % $N_{incorr}$ | | $S_n$ (Response Factors) | | |
|---|---|---|---|---|---|---|---|
| Analyte (n) | Mixture 1 | Mixture 2 | Mixture 1 | Mixture 2 | Mixture 1 | Mixture 2 | Average 1 & 2 |
| Methylene Chloride | 41.1 | 53.9 | 47.1 | 50.6 | 1.15 | 0.949 | 1.05 |
| Vinylidene Chloride | 28.4 | 18.7 | 43.0 | 22.0 | 1.51 | 1.18 | 1.35 |
| Ethylene Dichloride | 30.5 | 27.7 | 9.87 | 7.17 | 0.324 | 0.259 | 0.292 |

TABLE 3

Comparison of Concentration Estimates for Unbiased and Biased Data

| | Standards | | Unbiased | | Biased | |
|---|---|---|---|---|---|---|
| Analyte (n) | Mixture 1 | Mixture 2 | Mixture 1 | Mixture 2 | Mixture 1 | Mixture 2 |
| Methylene Chloride | 41.1 | 53.9 | 40.6 | 54.1 | 58.9 | 85.0 |
| Vinylidene Chloride | 28.3 | 18.6 | 28.8 | 18.3 | 44.5 | 33.8 |
| Ethylene Dichloride | 30.5 | 27.8 | 30.6 | 27.6 | −3.41 | −18.8 |

TABLE 4

$F_m$ Mass Dependent Correction Factors

| m/z (m) | Check-Gas | Surrogate Standard |
|---|---|---|
| 49 | 1.00 | 1.11 |
| 51 | 1.03 | 1.13 |
| 61 | 1.12 | 1.25 |
| 63 | 1.10 | 1.28 |
| 84 | 1.35 | 1.53 |
| 86 | 1.38 | 1.56 |
| 88 | 1.35 | 1.58 |
| 96 | 1.50 | 1.67 |
| 98 | 1.53 | 1.70 |
| 100 | 1.50 | 1.73 |
| 102 | 1.32 | 1.75 |

TABLE 5

Concentration Estimates for Biased Data to which Transfer Function was Applied

| | Standards | | Check-Gas Method | | Surrogate Method | |
|---|---|---|---|---|---|---|
| Analyte | Mixture 1 | Mixture 2 | Mixture 1 | Mixture 2 | Mixture 1 | Mixture 2 |
| Methylene Chloride | 41.1 | 53.9 | 41.0 | 54.2 | 40.5 | 53.2 |
| Vinylidene Chloride | 28.3 | 18.6 | 28.7 | 18.3 | 28.5 | 17.9 |
| Ethylene Dichloride | 30.5 | 27.8 | 30.3 | 27.5 | 30.9 | 28.6 |

EXAMPLE 2

The following example demonstrates a method using a surrogate standard to estimate the correction needed at each individual m/z in the aforementioned quantitative model, which is the value of a transfer function at the respective m/z's. As with example 1, the method makes use of a standard that is measured at the time the calibration model is constructed and makes use of an equivalent standard at a later time after mass discrimination has affected the instrumental response to determine a transfer function to apply to the data in the calibration model.

Figure 2A:
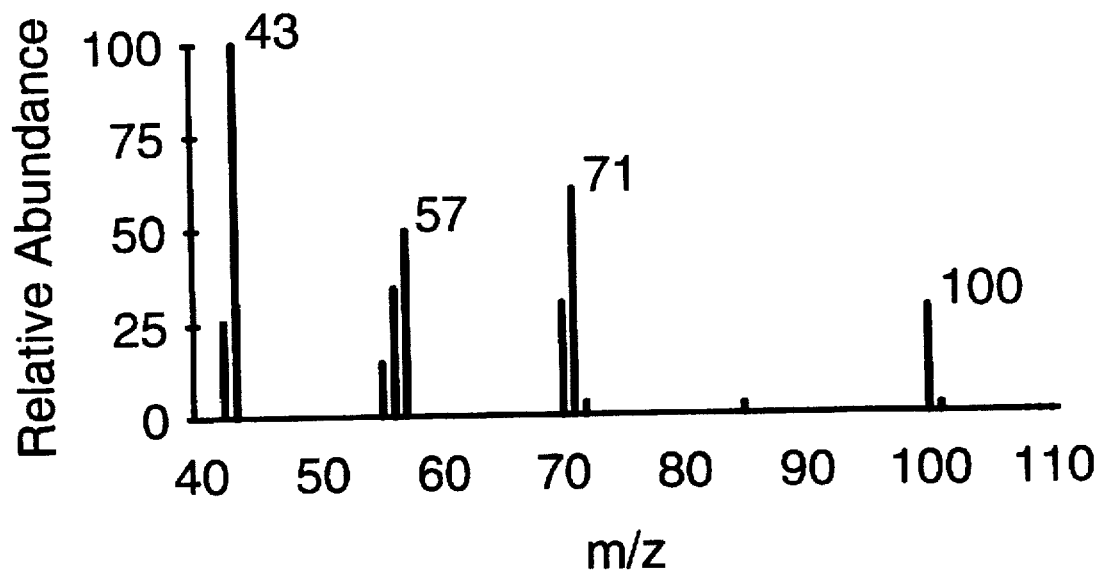
FIGS. 2A and 2B each show a mass spectrum of n-heptane.
Figure 2B:
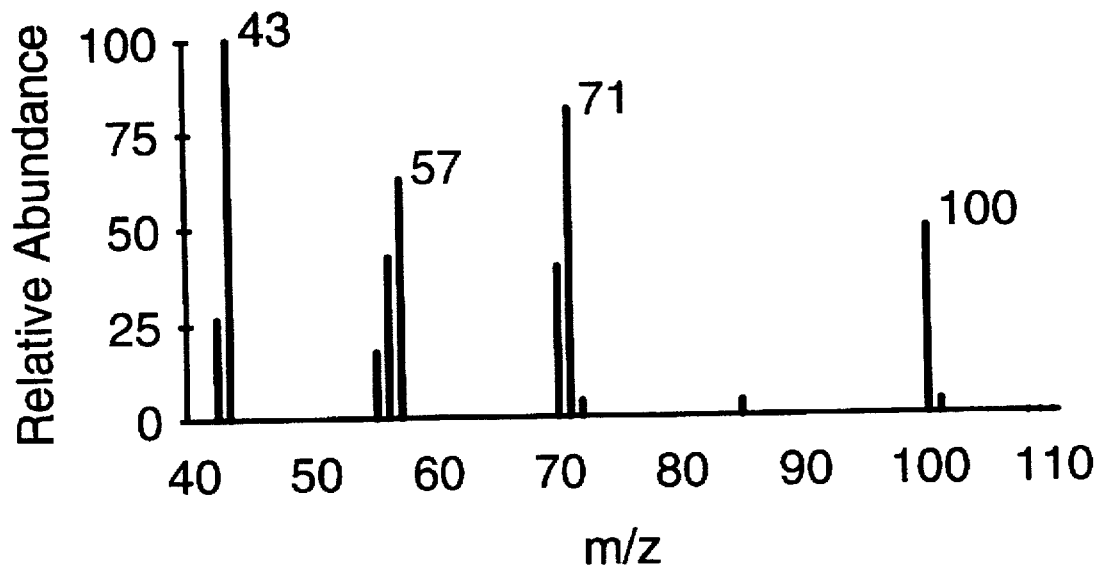

For many quantitative calibration situations it is not always possible to use a check-gas, particularly when analyte stability, toxicity, or economics are of a concern. In such cases, it may be possible to use the mass spectrum of a surrogate component (i.e., a component that does not directly map all ions being measured) to model the change in bias and transmission observed in mass spectra and generate an F matrix using a mathematical function. Mass spectra obtained from a quadrupole mass spectrometer configured with a capillary inlet and an electron multiplier detector are shown in FIGS. 2A and 2B. In this example, the spectra of neat n-heptane shown in FIG. 2 were used to correct the same three component model discussed in Example 1. The difference between this method and the previous method is that classical least squares is used to estimate transmission correction factors for the different m/z's used in the model. Heptane was chosen as a surrogate standard since it gave abundant mass fragmentation across the mass range being utilized by the three component model. As in the preceding check-gas approach, the ratio of the intensities of the (biased/unbiased) m/z values were used to model mass transmission. Table 6 shows the selected m/z values used, the intensity of each peak at those m/z values for the mass spectra shown in FIG. 2. In this example, FIG. 2A represents an unbiased spectrum of heptane and FIG. 2B represents a biased spectrum of heptane. Table 6 also shows the ratios of the peaks used to model the transmission changes. A least squares fit of this data gives equation (17) with a regression coefficient of 0.98. Equation (17) was used to generate the F matrix values (surrogate standard) in Table 4. Only the major ions of n-heptane were used to ensure consistency in the signal-to-noise in determining the transfer function.

$$F_m = 0.0122 \times (m/z)_m + 0.510 \quad (17)$$

When the correction factors were substituted into the quantitative model using the R and S matrices developed in Example 1, the concentration results predicted for the severely biased response in the mixture gave results shown in Table 5 that were within 4% relative error. As in the check-gas approach in Example 1, this computation did not alter the R or S matrix.

TABLE 6

Heptane - Surrogate Standard

| m/z | Heptane Unbiased | Heptane Biased | Ratio Unbiased/Biased |
|---|---|---|---|
| 43 | 100.0 | 100.0 | 1.00 |
| 57 | 49.4 | 62.7 | 1.27 |
| 71 | 60.0 | 81.1 | 1.31 |
| 100 | 28.4 | 48.9 | 1.72 |

EXAMPLE 3

The following example describes a method to enhance existing library searching capabilities. This example uses the surrogate approach discussed in Example 2, however, using the check-gas approach as discussed in Example 1 would also be valid. Example 3 demonstrates that the correlation between two spectra of n-heptane, taken at two different times, improves after applying a transformation using a surrogate standard to minimize the differences in bias between the 'unknown' spectrum and a library reference spectrum.

Let the reference spectrum of a standard stored in a library and the unknown sample spectrum be described by the matrices L and U, respectively. The reference spectrum can be related to the unknown spectrum by equation (18), $$FL = U \quad (18)$$

where F describes the relationship between a library reference spectrum and an unknown spectrum. Implied in this assumption is that a data array is common to both the library and the working instrument used to collect the unknown sample spectrum. In other words, the spectral data stored in the library for one analyte is standardized with respect to the spectral data of other analytes in the library, and the library includes a spectrum representative of a component in the unknown sample. The unknown sample spectrum in this example may be described as an experimental data array obtained on a working instrument. The spectrum of the unknown sample should be obtained in the same time frame as the spectrum of an equivalent standard in the library so that the transfer function matrix, F, can account for biases between data in the library and data from the instrument used to collect the unknown spectrum.

The F matrix was generated, using the surrogate approach, from both biased (t=t) and unbiased (t=0) spectra taken of a mixture of 53.9% methylene chloride, 18.7% vinylidene chloride, and 27.7% ethylene dichloride by weight (Table 7). The spectra of n-heptane shown in FIG. 2 show the extent of instrument bias between time t=0 (FIG. 2A) and time t=t (FIG. 2B). The spectral data in column one was obtained in the same time frame (time t=0) that a reference mass spectrum of n-heptane was generated for the library, as shown in FIG. 2A. Both may be considered spectral data of standards which are known components and are stored in a library. Because the spectral data for the mixture and for n-heptane were acquired in the same time frame under two separate circumstances (t=0 and t=t), the transfer function, F, relating L to U for the mixture should be the same as the transfer function relating L to U for n-heptane. Thus, a transfer function only needs to be determined for either n-heptane or for mixture 2 and that transfer function can be applied to the other. For purposes of this example, the spectrum of n-heptane in FIG. 2B is treated as an unknown. This example not only demonstrates the use of enhanced library searching capabilities, but also demonstrates that a mixture may be used as a standard whose reference spectrum is stored in a library; as long as the spectral data in the library are standardized with respect to each other and with respect to the unknown sample spectrum, the time frame to which data are standardized does not matter.

In this example, FIG. 2B represents a mass spectrum of n-heptane which was obtained in the same time frame (t=t) as the spectral data for mixture 2 which is shown in column two of Table 7. Because both sets of spectral data (FIG. 2B for n-heptane and column two of Table 7 for mixture 2) are taken in the same time frame (time t=t), either set could be considered the spectral data of an unknown.

In the time frame (t=0), the mixture is referred to as a standard; in the time frame (t=t), the mixture is referred to as an equivalent standard as defined in the terms above. The spectrum of n-heptane shown in FIG. 2B, which was obtained in the same time frame as the equivalent standard (t=t) may be referred to as a biased sample spectrum.

A least squares fit of the ((biased mixture, t=t)/(unbiased mixture, t=0)) ratio of the major ions of the mixture as a function of m/z were used to generate equation (19) as shown below. Equation (19) models the instrument bias using the observed changes in the spectrum of the equivalent standard as compared to the spectrum of a standard. Equation (19) determines the mathematical correction utilized in the matrix, F, relating L and U for each m/z in a spectral region of interest common to the library entries and unknown spectra.

$$F_m = 0.0102 \times (m/z)_m + 0.489 \quad (19)$$

In the case where n-heptane (as represented by FIG. 2B) is the unknown, Equation (19) may be used to transform the library entry for the mass spectrum of n-heptane (as represented by FIG. 2A) to reflect instrumental biases in the unknown spectrum, FIG. 2B. Table 8 shows that applying a transformation increases the correlation between the library spectrum and the sample spectrum of n-heptane.

Enhanced library searching may also be performed by transforming the unknown spectrum rather than the entire set of library spectra to limit the amount of spectral transformation required. This may be represented by equation (20) which is solved in a manner similar to the above example.

$$L = FU \quad (20)$$

For large libraries, this may be the preferred application since it will limit the amount of spectral transformations required before launching a library search.

TABLE 7

| m/z | Mixture t = 0 | Mixture t = t | Ratio t = t/t = 0 |
|-----|---------------|---------------|-------------------|
| 49  | 100.0         | 100.0         | 1.00              |
| 51  | 30.1          | 30.9          | 1.03              |
| 61  | 42.5          | 47.4          | 1.12              |
| 63  | 18.3          | 20.2          | 1.10              |
| 84  | 70.9          | 96.0          | 1.35              |
| 86  | 44.3          | 61.2          | 1.38              |
| 88  | 6.8           | 9.0           | 1.32              |
| 96  | 23.3          | 35.0          | 1.50              |
| 98  | 19.8          | 30.2          | 1.53              |
| 100 | 5.4           | 8.1           | 1.50              |

TABLE 8

Heptane Spectra

| m/z | Unknown obtained at t = t (FIG. 2B) | Library Entry t = 0 (FIG. 2A) | Library Entry Corrected to t = t | Library Entry Corrected to t = t & Normalized |
|-----|-------------------------------------|-------------------------------|----------------------------------|-----------------------------------------------|
| 42  | 25.1                                | 26.5                          | 24.3                             | 26.2                                          |
| 43  | 100.0                               | 100.0                         | 92.9                             | 100.0                                         |
| 55  | 17.4                                | 14.5                          | 15.2                             | 16.4                                          |
| 56  | 42.5                                | 34.4                          | 36.5                             | 39.3                                          |
| 57  | 62.7                                | 49.4                          | 53.0                             | 57.1                                          |
| 70  | 39.6                                | 30.4                          | 36.6                             | 39.4                                          |
| 71  | 81.1                                | 60.0                          | 72.9                             | 78.5                                          |
| 72  | 4.1                                 | 3.1                           | 3.8                              | 4.1                                           |
| 85  | 3.9                                 | 2.8                           | 3.8                              | 4.1                                           |
| 100 | 48.9                                | 28.4                          | 42.9                             | 46.2                                          |
| Correlation of unknown with Library Entry | | 0.966 | 0.998 | 0.998 |

What is claimed is:

1. A method of creating a library of standardized spectral data comprising the steps of:

(a) acquiring at least one reference spectrum over a spectral region of interest wherein each reference spectrum is representative of the spectrum of a standard, each reference spectrum being referred to as unbiased reference spectrum, said unbiased reference spectrum being stored and retrievable;

(b) acquiring at least one working spectrum over a corresponding spectral region on a working instrument, each working spectrum being representative of the spectrum of an equivalent standard and each being referred to as a biased working spectrum;

(c) deriving a transfer function from the unbiased reference spectra and the biased working spectra, the transfer function mathematically equates the biased working spectra to the unbiased reference spectra;

(d) during the same time interval as step (b), acquiring a spectrum of an additional standard on the working instrument over the corresponding spectral region, the spectrum of the additional standard being referred to as a biased spectrum of the additional standard;

(e) applying the transfer function of step (c) to the biased spectrum of the additional standard to obtain an unbiased reference spectrum of the additional standard; and (f) storing at least a portion of the unbiased reference spectrum of the additional standard in the library.

2. The method of claim 1 wherein the working spectra and the reference spectra are collected on separate instruments.

3. The method of claim 1 wherein the spectral data in the library comprises spectra having discrete peaks.

4. The method of claim 1 wherein the spectral data in the library comprises spectra having broadened peaks.

5. The method of claim 1 wherein the additional standard comprises a known compound of a known concentration such that the amount of the known concentration is retrievable.

6. The method of claim 1 wherein steps (b) through (f) are repeated.

7. The method of claim 1 wherein steps (d) through (f) are repeated.

8. A method of identifying a sample, said method comprising the steps of:

(a) acquiring a standardized library of reference spectra from a group of standards wherein the library of reference spectra is representative of the spectra of said group of standards, each spectrum in the library of reference spectra being referred to as an unbiased reference spectrum, said unbiased reference spectra being stored and retrievable;

(b) acquiring a sample spectrum; and (c) searching the library of reference spectra for a match with the sample spectrum, wherein the standardized library of reference spectra is acquired by the method of claim 1.

9. A method of identifying a sample, said method comprising the steps of:

(a) acquiring a standardized library of reference spectra from a group of standards wherein the library of reference spectra is representative of the spectra of said group of standards, each spectrum in the library of reference spectra being referred to as an unbiased reference spectrum, said unbiased reference spectra being stored and retrievable;

(b) acquiring an unbiased sample spectrum; and (c) searching the library of reference spectra for a match with the sample spectrum, wherein the unbiased sample spectrum is acquired by the steps of:

(i) acquiring at least one working spectrum over a spectral region of interest on a working instrument, each said working spectrum being representative of a spectrum of an equivalent standard and being referred to as a biased working spectrum, each said equivalent standard being selected from said group of standards;

(ii) deriving a transfer function from the biased working spectra and the unbiased reference spectra, the transfer function mathematically equates the working spectra to the corresponding unbiased reference spectra;

(iii) during the same time interval as step (i), acquiring a biased sample spectrum of the sample on the working instrument; and (iv) applying the transfer function of step (ii) to the biased sample spectrum to obtain an unbiased sample spectrum.

10. A method of identifying a sample, said method comprising the steps of:

(a) acquiring a standardized library of reference spectra from a group of standards wherein the library of reference spectra is representative of the spectra of said group of standards, each spectrum in the library of reference spectra being referred to as an unbiased reference spectrum, said unbiased reference spectra being stored and retrievable;

(b) acquiring at least one working spectrum over a corresponding spectral region on a working instrument, each said working spectrum being representative of the spectrum of an equivalent standard and being referred to as a biased working spectrum, each said equivalent standard being selected from said group of standards;

(c) deriving a transfer function from the biased working spectra and the unbiased reference spectra, the transfer function mathematically equates the working spectra to the unbiased reference spectra;

(d) during the same time interval as step (b), acquiring a biased sample spectrum of the sample on the working instrument over the corresponding spectral region;

(e) applying the transfer function of step (c) to the biased sample spectrum to obtain an unbiased sample spectrum; and (f) searching the standardized library of reference spectra for a match with the unbiased sample spectrum to aid in the identification at least one component in the sample giving rise to said sample spectrum.

11. The method of claim 10 wherein at least one standard in the group of standards comprises a known compound of known concentration, and the concentration of at least one component in the sample is determined.

* * * * *